United States Patent
Bian et al.

(10) Patent No.: US 9,731,096 B2
(45) Date of Patent: Aug. 15, 2017

(54) CATHETER OR GUIDE WIRE MANIPULATING DEVICE FOR VASCULAR INTERVENTION

(71) Applicant: INSTITUTE OF AUTOMATION, CHINESE ACADEMY OF SCIENCES, Haidian District, Beijing (CN)

(72) Inventors: Guibin Bian, Beijing (CN); Zengguang Hou, Beijing (CN); Xiaoliang Xie, Beijing (CN); Long Cheng, Beijing (CN); Min Tan, Beijing (CN); Zhenqiu Feng, Beijing (CN); Xiaohu Zhou, Beijing (CN)

(73) Assignee: INSTITUTE OF AUTOMATION, CHINESE ACADEMY OF SCIENCES, Hadian District, Beijing (CN)

( * ) Notice: Subject to any disclaimer, the term of this patent is extended or adjusted under 35 U.S.C. 154(b) by 125 days.

(21) Appl. No.: 14/770,223

(22) PCT Filed: Jun. 25, 2013

(86) PCT No.: PCT/CN2013/077883
§ 371 (c)(1),
(2) Date: Oct. 30, 2015

(87) PCT Pub. No.: WO2014/127598
PCT Pub. Date: Aug. 28, 2014

(65) Prior Publication Data
US 2016/0051794 A1    Feb. 25, 2016

(30) Foreign Application Priority Data
Feb. 25, 2013 (CN) .......................... 2013 1 0058143

(51) Int. Cl.
*A61M 31/00* (2006.01)
*A61M 25/01* (2006.01)
(Continued)

(52) U.S. Cl.
CPC ..... *A61M 25/0105* (2013.01); *A61B 19/2203* (2013.01); *A61B 34/20* (2016.02);
(Continued)

(58) Field of Classification Search
CPC ............... A61B 34/20; A61B 19/2203; A61B 2019/2211; A61M 25/0105; A61M 25/0113; A61M 25/09041
(Continued)

(56) References Cited

U.S. PATENT DOCUMENTS

| 2004/0254566 A1* | 12/2004 | Plicchi | A61B 34/37 606/1 |
| 2009/0105645 A1* | 4/2009 | Kidd | A61M 25/0113 604/108 |
| 2011/0264038 A1* | 10/2011 | Fujimoto | A61B 17/12022 604/95.01 |

FOREIGN PATENT DOCUMENTS

| CN | 101933837 A | 1/2011 |
| CN | 102596306 A | 7/2012 |

(Continued)

OTHER PUBLICATIONS

International Search Report for corresponding International Patent Application No. PCT/CN2013/077883 mailed Dec. 5, 2013.

*Primary Examiner* — Jason Flick
(74) *Attorney, Agent, or Firm* — Merchant & Gould P.C.

(57) ABSTRACT

A catheter or guide wire manipulating device for vascular intervention is provided, comprising a thumb component (3), a forefinger component (4), a driving component (1) and a catheter/guide wire support component (2); the thumb (Continued)

component comprises a roller (7) configured to advance or retreat the catheter/guide wire; the thumb component (3) is configured to drive the catheter/guide wire to rotate clockwise or counterclockwise through a combination motion of the components; the forefinger component (4) is configured to cooperate with the thumb component (3) to implement the rotation and the advancement of the catheter/guide wire by moving manually away from the thumb component, and returning by a pull force of a spring (23) after being released; the driving component (1) is configured to drive the thumb component (3) and the forefinger component (4); the catheter/guide wire support component (2) comprises a Y adapter fixation configured to install a Y adapter and an entry support configured to support and guide the catheter/guide wire into a mechanism.

6 Claims, 5 Drawing Sheets

(51) Int. Cl.
    *A61M 25/09*     (2006.01)
    *A61B 19/00*     (2006.01)
    *A61B 34/20*     (2016.01)

(52) U.S. Cl.
    CPC .. *A61M 25/0113* (2013.01); *A61M 25/09041* (2013.01); *A61B 2019/2211* (2013.01)

(58) Field of Classification Search
    USPC .................................................. 604/95.01
    See application file for complete search history.

(56) References Cited

FOREIGN PATENT DOCUMENTS

| | | |
|---|---|---|
| CN | 103083783 A | 5/2013 |
| CN | 103083784 A | 5/2013 |
| CN | 103157170 A | 6/2013 |

* cited by examiner

CATHETER OR GUIDE WIRE MANIPULATING DEVICE FOR VASCULAR INTERVENTION

This application is a National Stage Application of PCT/CN2013/077883, filed 25 Jun. 2013, which claims benefit of Ser. No. 201310058143.3, filed 25 Feb. 2013 in China and which applications are incorporated herein by reference. A claim of priority is made to each of the above disclosed applications.

TECHNICAL FIELD

The disclosure generally relates to a technical field of medical equipments, and more particularly, to a catheter or guide wire manipulating device for vascular intervention.

BACKGROUND

Vascular intervention may be implemented by, under a guidence of a digital subtraction angiography (DSA) system, manipulating a catheter inside human vessels with a surgeon and treating deseases to realize angiostegnosis dialation and angioplasty.

Conventionally, the vascular intervention is mainly done manually by the surgeons. Main disadvantages include 1) long time operation under the X-ray imaging will cause severe damage to the surgeons' health; 2) the conventional operation method requires high manipulation skills, long training time, and has high risk; and 3) factors, such as complicated operations, long operation time and fatigue of surgeons and unstable operation factors, will directly affect a quality of operation and latter patients' recovery. These shortcomings limit a further application of the vascular intervention. Therefore, it is needed a solution to adopt a robotic technology to the vacular intervention.

To solve above problems, Hansen Meidical improved a structure of catheter and then developed an active catheter system. However, the size of the developed catheter is too bigger and this narrows its application. Beihang University made an advancing catheter mechanism, but its assembly, disassembly and sterilization are inconvenient. Institute of Automation, Chinese Academy of Sciences designed an advancing catheter mechanism to imitate human's manipulation, but it cannot allow the catheter to advance continuously. In addition, it is unable to allow simultaneous advancement and rotation of a catheter/guide wire. Therefore the present disclosure is directed to address above problems and propose a catheter manipulating device.

SUMMARY

In view of the foregoing, the present disclosure provides a catheter or guide wire manipulating device capable of driving the catheter/guide wire to implement an advancement motion, a rotation motion or a simultaneous combination of the both inside vessels.

A catheter or guide wire manipulating device for vascular intervention is provided, comprising a thumb component, a forefinger component, a driving component and a catheter/guide wire support component; the thumb component comprises a roller configured to advance or retreat the catheter/guide wire; the thumb component is configured to drive the catheter/guide wire to rotate clockwise or counterclockwise through a combination motion of the thumb component and the forefinger component; the forefinger component is configured to cooperate with the thumb component to implement the rotation and advancement of the catheter/guide wire by moving the forefinger component manually away from the thumb component, and returning by a pull force of a spring after being released; the driving component is configured to drive the thumb component and the forefinger component; the catheter/guide wire support component comprises a Y adapter fixation configured to install a Y adapter and an entry support configured to support and guide the catheter/guide wire into the disclosure device.

In a possible implementation, the catheter or guide wire manipulating device is configured to manipulate the catheter/guide wire to implement the advancement motion and the rotation motion along two directions respectively; the advancement motion of catheter/guide wire is attached to the rotation motion of the catheter/guide wire.

In a possible implementation, rollers of the forefinger component and the thumb component are provided with rubber covers respectively so that a deformation is formed on the rubber cover as the two components are tightly pressed by the proper pull force of the spring. Thus a contact area between rubber covers and the catheter/guide wire is increased. The increased contact area will improve a stability of the catheter/guide wire manipulation via a friction.

In a possible implementation, the thumb component includes a roller, a rubber cover, a drive shaft, a bearing unit, a motor frame, a coupling and an advancing motor; the advancing motor is fixed to the motor frame with bolts; a motor output shaft of the advancing motor is connected to the drive shaft via a coupling; the drive shaft is supported by the bearing unit; one end of the drive shaft is connected to the roller via a thread; the rubber cover is made of material of rubber and mounted on the roller by an interference fit.

In a possible implementation, the roller of the thumb component is configured to be rotated to make the catheter/guide wire advance or retreat by making the drive shaft rotate by the coupling, driving the roller of the thumb component to rotate by a rotation of the advancing motor output shaft and driving the catheter/guide wire to advance or retreat with the spring's pull force between the rubber cover of the thumb component and the rubber cover of the forefinger component.

In a possible implementation, the catheter/guide wire is configured to rotate clockwise or counterclockwise via a combined motion of the thumb component and the forefinger component by connecting the roller, the rubber cover, the drive shaft, the bearing unit, the motor frame, the coupling, and the advancing motor of the thumb component as a whole part to the driving component through a connecting plate, moving the whole part linearly up and down with a guidance of guide rails, while driving the roller of forefinger component by the driving component to move linearly in an opposite direction to a motion direction of the whole part.

In a possible implementation, the forefinger component includes a roller, a rubber cover, a roller shaft, a bearing unit, a forefinger component pedestal, a spring, a horizontal guide rail, a forefinger component base board, a vertical guide rail and a connecting plate; the rubber cover is fixed to the roller by an interference fit; the roller is connected fixedly to the roller shaft through a thread; the roller shaft is supported fixedly by the bearing unit fixed on the forefinger component base board by the guide rail; the forefinger component base board is connected to a screw rod output through the connecting plate and to a fixed pedestal of the driving component through the guide rails; the forefinger component pedestal is configured to tightly press the roller of the forefinger component and the roller of the thumb component through a pull force of a spring.

With a position relationship and a movement relationship among the thumb component, the forefinger component, the driving component and the catheter/guide wire support component, the catheter or guide wire manipulating device for vascular intervention according to the present disclosure is established to realize the advancement, the rotation and the combined motion of the catheter/guide wire. The surgeons' workload and working duration in a radiation environment may be reduced and an accuracy of the catheter/guide wire movement inside human vessels may be improved.

DETAILED DESCRIPTION OF EMBODIMENTS

Figure 1:
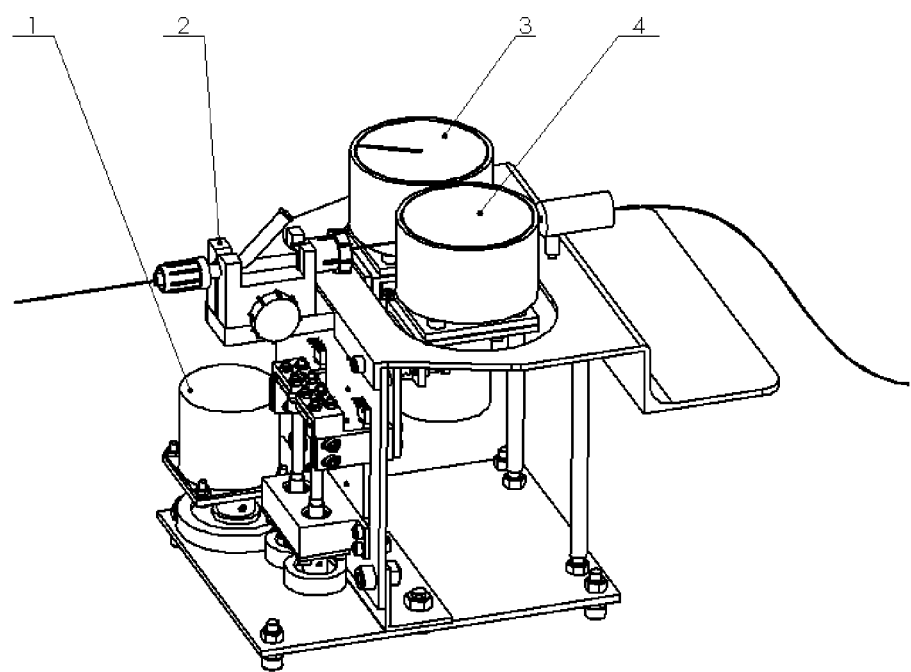
FIG. 1 shows an overall structure of the catheter or guide wire manipulating device for vascular intervention according to an embodiment of the disclosure.

For the object, technical solutions and advantages of the disclosure to be more clear and apparent, the disclosure will further elucidated in conjunction with detailed embodiments and with reference to accompanying drawings in the following.

Reference Signs:

driving component 1, catheter/guide wire support component 2, thumb component 3, forefinger component 4, connecting plate 5, guide rail 6, roller 7, rubber cover 8, bearing unit 9, drive shaft 10, coupling 11, motor frame 12, advancing motor 13, connecting plate 14, forefinger component base board 15, horizontal guide rail 16, vertical guide rail 17, roller 18, rubber cover 19, bearing unit 20, forefinger component pedestal 21, roller shaft 22, spring 23, nut connecting frame 24, nut connecting frame 25, screw rod 26, screw rod 27, bearing unit 28, base board 29, pinion 30, pinion 31, gear 32, motor frame 33, rotating motor 34, Y adapter fixation 35, top plate 36, entry support 37.

FIG. 1 shows a structure of the catheter or guide wire manipulating device for vascular intervention according to an embodiment of the disclosure.

As shown in FIG. 1, the manipulating device may include a thumb component 3, a forefinger component 4, a driving component 1, and a catheter/guide wire support component 2 and drive the catheter/guide wire to advance, rotate or advance while rotate inside the human vessels. The thumb component 3 includes a roller to make the catheter/guide wire advance or retreat. The thumb component 3 and the forefinger component 4 can drive the catheter/guide wire to rotate clockwise and counterclockwise through a combination motion of two fingers. The forefinger component 4 cooperates with the thumb component 3 to realize the rotation and the advancement of the catheter/guide wire. The forefinger component 4 can be moved manually away from the thumb component 3. After being released, the forefinger component 4 returns due to the pull force of the spring. The driving component 1 is configured to move the thumb component 3 and the forefinger component 4. The catheter/guide wire support component 2 includes a Y adapter fixation and an entry support. The Y adapter fixation is used to install a Y adapter quickly, and the entry support can support and guide the catheter/guide wire effectively into the mechanism. The catheter or guide wire manipulating device drives the catheter/guide wire to move along two directions: advancement and rotation. An advancement mechanism of the catheter/guide wire is attached to the rotation mechanism. When clamping the catheter/guide wire, the forefinger component 4 can be moved manually away from the thumb component 3. After being released, the forefinger component 4 returns by the pull force of the spring. Rubber covers are mounted on both rollers of the forefinger component 4 and the thumb component 3, respectively. Since two components are tightly pressed by the proper pull force of the spring, a deformation is formed on the rubber cover so as to increase the contact area between rubber covers and the catheter/guide wire. The increased contact area will improve the stability of manipulating the catheter/guide wire via the friction.

Figure 2:
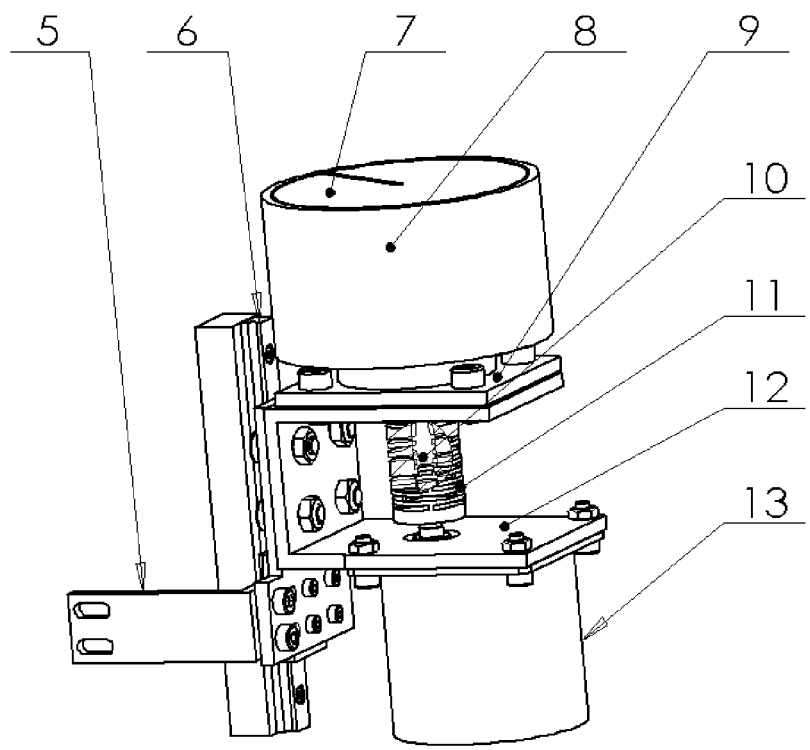
FIG. 2 shows a structure of the thumb component of the catheter or guide wire manipulating device for vascular intervention according to the embodiment of the disclosure.

FIG. 2 shows a structure of the thumb component 3. Referring to FIG. 2, the thumb component may include a roller 7, a rubber cover 8, a drive shaft 9, a motor frame 12, a coupling 11, an advancing motor 13, a guide rail 6, and a connecting plate 5. The advancing motor 13 and the motor frame 12 are fixed together with bolts. An output shaft of advancing motor 13 is connected to the drive shaft 10 by the coupling. The drive shaft 10 is supported by the bearing unit 9 and ends of the drive shaft 10 are fixedly connected to the roller 7 by a thread. Rubber cover 8 may be made of rubber and mounted on the roller 7 by an interference fit.

Roller 7 of the thumb component makes the catheter/guide wire advance or retreat by rotating the drive shaft 10 with the output shaft of the advancing motor 13 through the coupling 11, driving the roller 7, and driving the catheter/guide wire to advance or retreat through a pressure between the rubber cover 8 and the rubber cover of the forefinger component 4.

The thumb component 3 and the forefinger component 4 can drive the catheter/guide wire to rotate in a clockwise or a counterclockwise direction through a combination motion of two fingers by connecting the roller 7, the rubber cover 8, the drive shaft 10, the bearing unit 9, the motor frame 12, the coupling 11 and the advancing motor 13 of the thumb component as a whole part to the driving component 1 through the connecting plate 5, moving the whole part linearly up and down with the guidance of guide rail 6 while driving the roller of the forefinger component 4 by the driving component 1 to move linearly in an opposite direction to a motion direction of the whole part.

Figure 3:
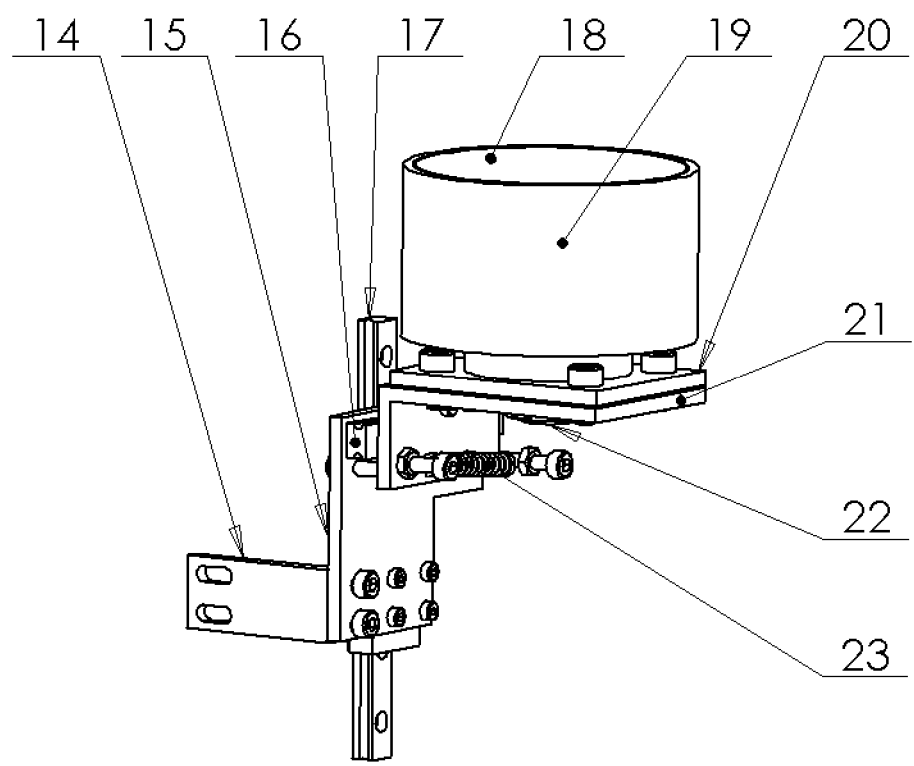
FIG. 3 shows a structure of the forefinger component of the catheter or guide wire manipulating device for vascular intervention according to the embodiment of the disclosure.

FIG. 3 shows a structure of forefinger component 4. Referring to FIG. 3, the forefinger component may include a roller 18, a rubber cover 19, a roller shaft 22, a bearing unit 20, a forefinger component pedestal 21, a spring 23, a horizontal guide rail 16, a forefinger component base board 15, a vertical guide rail 17 and a connecting plate 14.

The rubber cover 19 is made of elastic material (such as rubber) and fixed on roller 18 by an interference fit. The roller 18 is fixedly connected to the roller shaft 22 through a thread. The roller shaft 22 is supported by the bearing unit 20 fixed on the forefinger component base board 15 by the guide rails. The forefinger component base board 15 is connected to a screw rod output via the connecting plate 14 and to a fixed pedestal of the driving component 1 via the guide rail 17. The forefinger component pedestal 21 allows the roller 18 of the forefinger component and the roller of the thumb component to be tightly pressed by the pull force of a spring 23. The forefinger component 4 cooperates with the thumb component 3 to realize the rotation, the advancement and the combined motion of the catheter/guide wire. The advancement of the catheter/guide wire can be realized by the rotation of the roller 7 of the thumb component 3 when the roller 18 is tightly pressed on the roller 7 of the thumb component 3. When the screw rod of the driving component 1 drives the connecting plate 14, the roller 18 of the forefinger component 4 and the roller 7 of the thumb component 3 can move linearly along opposite directions. Then the catheter/guide wire may rotate in a clockwise direction or a counterclockwise direction.

Figure 4:
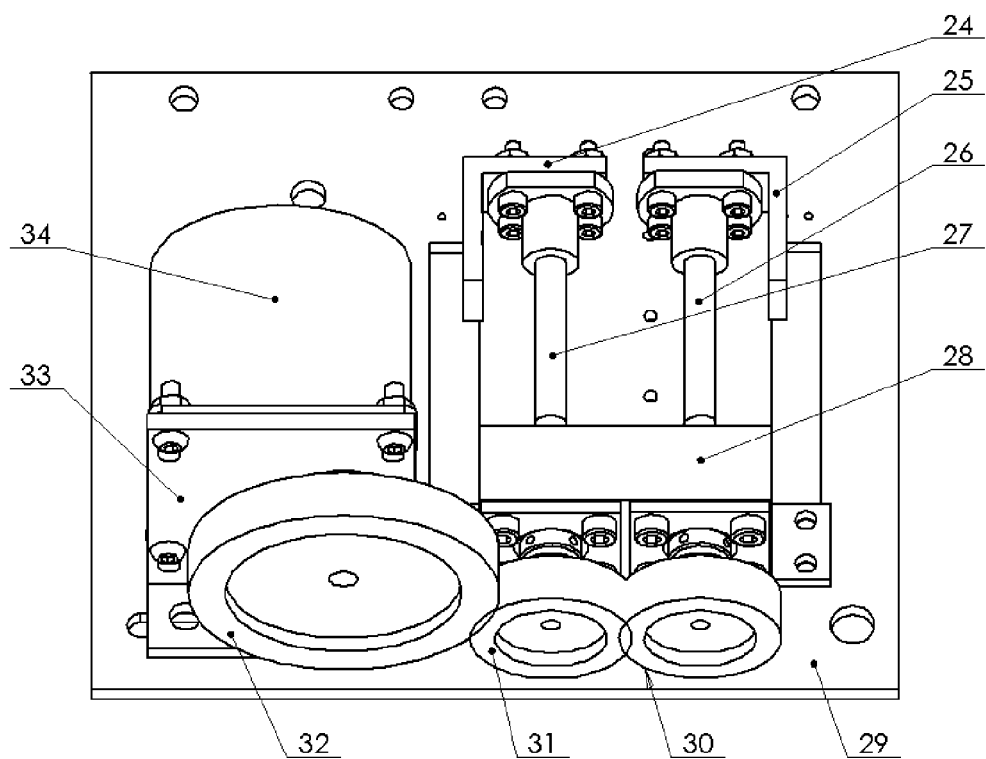
FIG. 4 shows a structure of the driving component of the catheter or guide wire manipulating device for vascular intervention according to the embodiment of the disclosure.

FIG. 4 shows a structure of the driving component 1. The driving component may include a rotating motor 34, a motor frame 33, a gear 32, a pinion 31, a pinion 30, a base board 29, a bearing unit 28, a screw rod 27, a screw rod 26, a nut connecting frame 25 and a nut connecting frame 24. The rotating motor 34 is connected to the motor frame 33 by bolts. The output shaft of motor 34 is fixedly connected to the gear 32. The pinion 31 is engaged with the gear 32, and the pinion 31 is engaged with the pinion 30. The pinion 31 is connected to the end of screw rod 27. The screw rod 26 and 27 are both supported by the bearing unit 28. The nut connection frames 24 and 25 are respectively connected to the nuts of screw rod 27 and 26. The screw pitch of the two screw rods 27 and 26 may be the same. The motor frame 33 and the bearing unit 28 are all fixed on the base board 29. The driving component 1 is used to drive the movement of the thumb component 3 and the forefinger component 4. The transmission is as follows. The output shaft of motor 34 drives the gear 32 to be rotated. Pinion 31 is engaged with the gear 32. Similarly, the pinion 31 is engaged with the pinion 30. Then the nuts of screw rod 27 and 26 allow linear movement along the opposite direction. The movement is transmitted to the thumb component 3 and the forefinger component 4 through the nut connecting frames 24 and 25.

Figure 5:
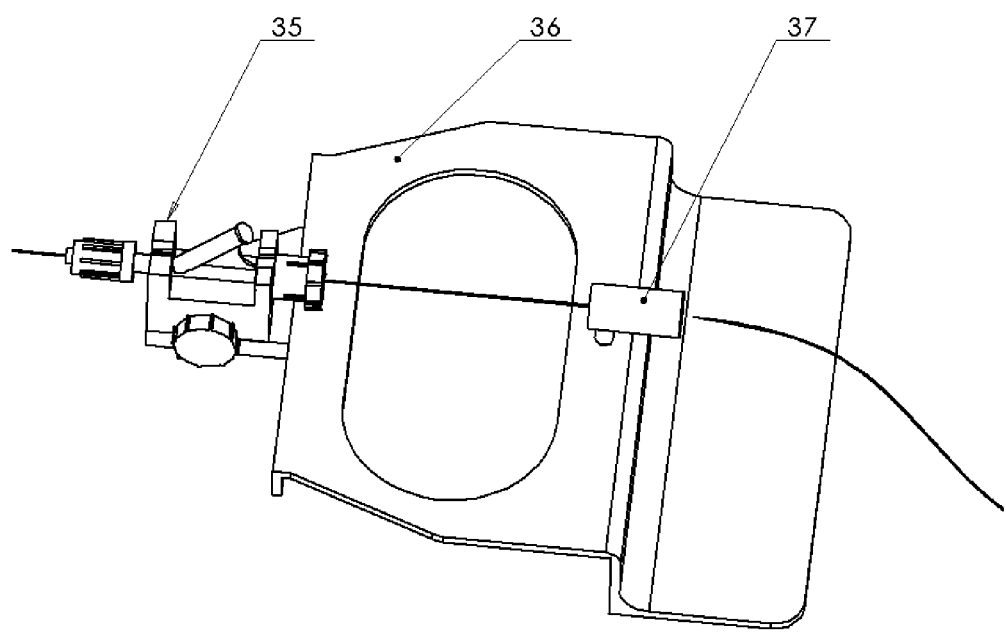
FIG. 5 shows a structure of the catheter/guide wire support component of the catheter or guide wire manipulating device for vascular intervention according to the embodiment of the disclosure.

FIG. 5 shows a structure of catheter/guide wire support component. The catheter/guide wire support component includes Y adapter fixation 35, an entry support 37 and a top plate 36. The Y adapter fixation 35 is configured to install a Y adapter quickly. The entry support is a hollow structure to support the catheter/guide wire when the catheter/guide wire is transmitted into the mechanism. When a Y adapter is loaded on the Y adapter fixation 35, both center lines of the Y adapter and the entry support 37 should be collinear.

The catheter or guide wire manipulating device drives the catheter/guide wire to move along two directions: advancement and rotation. The advancement driven by the advancing motor 13 of the catheter/guide wire is attached to the rotation driven by the rotating motor 34.

When clamping the catheter/guide wire, the roller 18 of the forefinger component 4 can be moved manually away from the roller 7 of the thumb component 3. After being released, the roller 18 and the roller 7 are tightly pressed by the pull force of spring 23.

The rubber cover 8 and 19 are respectively mounted on the roller 7 of the thumb component 3 and the roller 18 of the forefinger component 4 so that the deformation, which can increase the contact area between rubber covers and the catheter/guide wire, is formed due to two tightly-pressed components. Thus, the increased contact area improves the stability of manipulating the catheter/guide wire via the friction.

The advancement transmission of catheter/guide wire is as follows. The output shaft of the advancing motor 13 is connected to the roller shaft 10 of the thumb component through coupling 11. Then the roller shaft 10 drives the roller 7 of the thumb component to rotate while the catheter/guide wire is pressed by the roller shaft 18 of the thumb component through spring 23. Then the friction drives the catheter/guide wire to advance.

The rotation transmission of the catheter/guide wire is as follows. The rotation of rotating motor 34 is transmitted to the input of two screw rods (26 and 27) through a gear transmission (gear 32, pinions 31, 32) with the same speed but along opposite directions. The movement is transmitted to the guide rail 6 and the vertical guide rail 17, which are respectively connected to the connecting plate 5 of the thumb component and the connecting plate 14 of the forefinger component. Then the roller 7 of the thumb component and the roller 18 of the forefinger component move vertically along the opposite directions while the two rollers 7, 18 are pressed by the pull force of the spring and the friction drives the catheter/guide wire to rotate.

The rotating motor 34 and the advancing motor 13 can be controlled simultaneously because the two motions are structural decoupling. Therefore the simultaneous rotation motion and advancement motion of the catheter/guide wire are allowed.

In an application of medical sterilization, the roller 7 of the thumb component 3 and the roller 18 of the forefinger component 4 are respectively connected to the drive shaft 10 and the roller shaft 18 through the thread. That is to say, the rollers 7 and 18 can be easily disassembled. In practice, the surgeons can cover a layer of medical isolation membrane, and then install the rollers 7 and 18. The rollers 7 and 18 can be disposal. Therefore, the device is convenient for medical sterilization.

The above detailed embodiments describe the object, technical solutions and advantages of the disclosure in further detail. It shall be appreciated that the above contents are just detailed embodiments of the disclosure and are not intended to limit the disclosure. Any alternative, equivalent replacements, improvements, etc. made within the spirit and scope of the disclosure shall be encompassed by the scope of the disclosure.

What is claimed is:

1. A catheter or guide wire manipulating device for vascular intervention comprising a thumb component, a forefinger component, a driving component and a catheter/guide wire support component;

the thumb component comprises a roller configured to advance or retreat the catheter/guide wire; the thumb component is configured to drive the catheter/guide wire to rotate clockwise or counterclockwise by a combination motion of the thumb component and the forefinger component;

the forefinger component is configured to cooperate with the thumb component to implement the rotation and advancement of the catheter/guide wire by moving the forefinger component manually away from the thumb component, and the forefinger component returning by a pull force of a spring after being released;

the driving component is configured to drive the thumb component and the forefinger component; the driving component include a rotating motor, gears, pinions and screw rods, the rotating motor drives gears to rotate, the gears are engaged with the pinion correspondingly, nuts of the screw rods make a linear movement along opposite directions so that the linear movement is supplied to the thumb component and the forefinger component, respectively;

the catheter/guide wire support component comprises a Y adapter fixation configured to install a Y adapter and an entry support configured to support and guide the catheter/guide wire into a mechanism; the entry support has a hollow structure to support the catheter/guide wire when the catheter/guide wire is transmitted into the mechanism;

wherein rollers of the forefinger and thumb component are provided with rubber covers respectively so that a deformation is formed on the rubber cover as the two components are tightly pressed by the proper pull force of the spring and a contact area between rubber covers and the catheter/guide wire is increased, improving a stability of manipulating the catheter/guide wire via a friction.

2. The catheter or guide wire manipulating device according to claim 1, wherein the catheter or guide wire manipulating device is configured to manipulate the catheter/guide wire to implement advancement motion and rotation motion along two directions; the advancement motion of catheter/guide wire is attached to the rotation motion of the catheter/guide wire.

3. The catheter or guide wire manipulating device according to claim 1, wherein, the thumb component includes a roller, a rubber cover, a drive shaft, a bearing unit, a motor frame, a coupling and an advancing motor; the advancing motor is fixed to the motor frame with bolts; a motor output shaft of the advancing motor is connected to the drive shaft by a coupling; the drive shaft is supported by the bearing unit; ends of the drive shaft are connected to the roller by a thread; the rubber cover is made of material of rubber and mounted on the roller by an interference fit.

4. The catheter or guide wire manipulating device according to claim 3, wherein, the roller of the thumb component is configured to rotate to make the catheter/guide wire advance or retreat by making the drive shaft rotate through the coupling, driving the roller of the thumb component to rotate by a rotation of the advancing motor output shaft and driving the catheter/guide wire to be advanced or retreated with the spring's pull force between the rubber cover of the thumb component and the rubber cover of the forefinger component.

5. The catheter or guide wire manipulating device according to claim 4, wherein the catheter/guide wire is configured to rotate clockwise or counterclockwise via a combined motion of the thumb component and forefinger component by connecting the roller, the rubber cover, the drive shaft, the bearing unit, the motor frame, the coupling, and the advancing motor of the thumb component as a whole part to the driving component through a connecting plate, moving the whole part linearly up and down with a guidance of guide rails, while driving the roller of forefinger component by the driving component to move linearly in an opposite direction to a motion direction of the whole part.

6. The catheter or guide wire manipulating device according to claim 5, wherein the forefinger component includes a roller, a rubber cover, a roller shaft, a bearing unit, a forefinger component pedestal, a spring, a horizontal guide rail, a forefinger component base board, a vertical guide rail and a connecting plate; the rubber cover is fixed to the roller by an interference fit; the roller is connected fixedly to the roller shaft through a thread; the roller shaft is supported fixedly by the bearing unit fixed on the forefinger component base board by the guide rail; the forefinger component base board is connected to a screw rod output through the connecting plate and to a fixed pedestal of the driving component through the guide rails; the forefinger component pedestal is configured to tightly press the roller of the forefinger component and the roller of the thumb component through a pull force of a spring.

* * * * *